United States Patent [19]
Hutson

[11] Patent Number: 5,348,020
[45] Date of Patent: Sep. 20, 1994

[54] METHOD AND SYSTEM FOR NEAR REAL-TIME ANALYSIS AND DISPLAY OF ELECTROCARDIOGRAPHIC SIGNALS

[76] Inventor: William H. Hutson, 47 Grange Ave., P.O. Box 0221, Little Compton, R.I. 02837

[21] Appl. No.: 991,291

[22] Filed: Dec. 15, 1992

Related U.S. Application Data

[63] Continuation-in-part of Ser. No. 978,245, Nov. 18, 1992, Pat. No. 5,245,587, which is a continuation-in-part of Ser. No. 628,337, Dec. 14, 1990, Pat. No. 5,175,710.

[51] Int. Cl.$^5$ ................................................ A61B 5/04
[52] U.S. Cl. ...................................... 128/696; 128/699
[58] Field of Search ...................... 128/696, 699, 708; 364/413.06

[56] References Cited

U.S. PATENT DOCUMENTS

| | | | |
|---|---|---|---|
| 3,894,348 | 7/1975 | Fontaine | 367/127 |
| 4,422,459 | 12/1983 | Simson | 128/702 |
| 4,458,691 | 7/1984 | Netravali | 128/705 |
| 4,458,692 | 7/1984 | Simson | 128/705 |
| 4,492,235 | 1/1985 | Sitrick | 128/705 |
| 4,630,204 | 12/1986 | Mortara | 364/417 |
| 4,736,199 | 4/1988 | Chadwick et al. | 362/127 |
| 4,839,853 | 6/1989 | Deerwester et al. | 364/900 |
| 4,965,732 | 10/1990 | Roy, III et al. | 364/460 |
| 4,973,111 | 11/1990 | Haacke et al. | 324/309 |
| 4,995,011 | 2/1991 | Spiesberger | 367/127 |
| 5,001,747 | 3/1991 | Sexton | 379/410 |
| 5,010,504 | 4/1991 | Lee et al. | 364/574 |
| 5,031,155 | 7/1991 | Hsu | 367/25 |
| 5,109,863 | 5/1992 | Semmlow et al. | 310/329 |
| 5,175,710 | 12/1992 | Hutson | 367/135 |
| 5,245,587 | 9/1993 | Hutson | 367/100 |

OTHER PUBLICATIONS

Schmidt, "Multiple Emitter Location and Signal Parameter Estimation" Mar. 1986.
Carroll et al, "Models and Methods for Three-way Multidimensional Scaling", 1974.
Owsley, "Enhanced Minimum Variance Beamforming" Nov. 18, 1988.
Marple, "Digital Spectral Analysis" 1987.
Kung, "Warp Demo" Aug. 29, 1986.
Comon, "An Array Processing Technique Using the First Principal Component" 1988.
Chayka, "Project 96050 Automated Processing of Complex Signal Environments FY86 Final Report" Nov, 1987.
Weiss et al, "MIT Industrial Liason Program Report" Oct. 23, 1987.

(List continued on next page.)

*Primary Examiner*—Angela D. Sykes
*Assistant Examiner*—Scott M. Getzow
*Attorney, Agent, or Firm*—Hale and Dorr

[57] ABSTRACT

The multidimensional ECG processing and display system of the present invention is used with an electrocardiographic (ECG) monitoring system. Input ECG data from multiple, sequential time intervals is collected and formatted into a two-dimensional matrix. The two-dimensional matrix is decomposed using singular value decomposition (SVD) to obtain its corresponding singular values and singular vectors, a compressed form of the matrix. The singular vectors are analyzed and filtered to identify and enhance signal components of interest. Selected singular vectors are transformed into their frequency domain representations by the Fast Fourier Transform (FFT), or related techniques. Certain data elements in the two-dimensional matrix are enhanced or diminished by modifying the singular values within groups of singular vectors to enhance certain objects that are associated with the ECG data and to diminish other features within the data. The enhanced data is expanded back into its original form and features in the ECG data are displayed as opaque objects within a transparent data cube.

54 Claims, 11 Drawing Sheets

OTHER PUBLICATIONS

Callaerts et al, "On-Line Algorithm for Signal Separation Based on SVD" 1988.
Moody et al, "QRS Morphology Representation and Noise Estimation Using the Karhunen-Loeve Transform" 1990.
Breithardt et al, "Standards for Analysis of Ventricular Late Potentials Using High Resolution or Signal-Averaged Electrocardiography" 1991.
Winters et al, "A Practical Guide to Signal-Averaged Electrocardiography and Late Potential Analysis" 1990.
Simson, "Signal Averaging" 1987.
Winters et al, "Signal Averaging of the Surface QRS Complex Predicts Inductibility of Ventricular Tachycardia in Patients with Syncope of Unknown Origin: A Prospective Study" 1987.
Gomes et al, "A New Noninvasive Index to Predict Sustained Ventricular Tachycardia and Sudden Death in the First Year After Myocardial Infarction: Based on Signal-Averaged Electrocardiogram, Radionuclide Ejection Fraction and Holter Monitoring" 1987.
Gomes, "Clinical Uses of the Signal-Averaged Electrocardiogram" 1988.
Haberl et al, "Top-Resolution Frequency Analysis of Electrocardiogram with Adaptive Frequency Determination" 1990.

FIG. 14.1

| 22 | 26 | 31 | 33 | 31 | 26 | 22 | 5 | 167 | 7 | 18 | 20 | 20 | 22 | 26 | 31 | 39 | 46 | 48 | 42 | 31 | 29 | 29 | 29 | 26 |
|---|---|---|---|---|---|---|---|---|---|---|---|---|---|---|---|---|---|---|---|---|---|---|---|---|
| 26 | 31 | 37 | 39 | 37 | 31 | 26 | 5 | 199 | 8 | 21 | 23 | 24 | 26 | 31 | 37 | 47 | 55 | 58 | 50 | 37 | 34 | 34 | 34 | 32 |
| 30 | 35 | 41 | 44 | 41 | 35 | 29 | 6 | 225 | 8 | 24 | 26 | 26 | 29 | 35 | 41 | 53 | 62 | 65 | 56 | 41 | 38 | 38 | 38 | 35 |
| 29 | 35 | 42 | 44 | 41 | 35 | 30 | 6 | 223 | 9 | 23 | 27 | 27 | 30 | 35 | 42 | 53 | 62 | 65 | 56 | 41 | 38 | 38 | 38 | 35 |
| 26 | 31 | 36 | 39 | 36 | 31 | 25 | 5 | 196 | 7 | 21 | 23 | 23 | 26 | 30 | 36 | 46 | 54 | 57 | 49 | 36 | 34 | 33 | 33 | 31 |
| 22 | 26 | 30 | 32 | 30 | 26 | 21 | 4 | 164 | 7 | 17 | 20 | 19 | 22 | 25 | 30 | 38 | 45 | 47 | 41 | 30 | 28 | 28 | 28 | 26 |
| 20 | 24 | 28 | 30 | 28 | 24 | 20 | 4 | 152 | 6 | 16 | 18 | 18 | 20 | 24 | 28 | 36 | 42 | 44 | 38 | 28 | 26 | 26 | 26 | 24 |
| 22 | 27 | 31 | 34 | 31 | 27 | 22 | 5 | 169 | 7 | 17 | 21 | 20 | 23 | 26 | 32 | 40 | 47 | 49 | 42 | 31 | 29 | 29 | 29 | 27 |
| 26 | 32 | 38 | 40 | 37 | 32 | 27 | 5 | 203 | 8 | 22 | 23 | 25 | 26 | 33 | 37 | 48 | 56 | 59 | 51 | 37 | 35 | 35 | 35 | 32 |
| 30 | 36 | 41 | 44 | 41 | 35 | 29 | 6 | 225 | 9 | 23 | 27 | 26 | 30 | 35 | 42 | 53 | 62 | 65 | 56 | 41 | 38 | 38 | 38 | 36 |
| 29 | 35 | 41 | 44 | 41 | 35 | 29 | 6 | 222 | 8 | 24 | 26 | 27 | 29 | 35 | 40 | 53 | 61 | 64 | 55 | 41 | 38 | 38 | 38 | 35 |
| 25 | 30 | 36 | 38 | 36 | 31 | 26 | 5 | 193 | 8 | 20 | 24 | 22 | 26 | 30 | 36 | 46 | 54 | 56 | 48 | 36 | 33 | 33 | 33 | 31 |
| 21 | 26 | 30 | 32 | 30 | 26 | 21 | 4 | 163 | 6 | 18 | 19 | 20 | 21 | 26 | 29 | 39 | 45 | 47 | 41 | 30 | 28 | 28 | 28 | 26 |
| 20 | 24 | 28 | 30 | 28 | 24 | 20 | 4 | 152 | 7 | 15 | 19 | 19 | 21 | 24 | 29 | 36 | 42 | 44 | 38 | 28 | 26 | 26 | 26 | 24 |
| 22 | 27 | 32 | 34 | 32 | 27 | 23 | 4 | 172 | 6 | 19 | 19 | 19 | 21 | 22 | 31 | 41 | 47 | 50 | 43 | 32 | 29 | 29 | 29 | 27 |
| 27 | 32 | 38 | 41 | 38 | 33 | 27 | 6 | 205 | 8 | 22 | 25 | 24 | 27 | 33 | 38 | 49 | 57 | 60 | 52 | 38 | 35 | 35 | 35 | 33 |

← WAVEFORM STRUCTURE →

TIME HISTORY

METHOD AND SYSTEM FOR NEAR REAL-TIME ANALYSIS AND DISPLAY OF ELECTROCARDIOGRAPHIC SIGNALS

BACKGROUND OF THE INVENTION

This application is a continuation-in-part of U.S. Ser. No. 07/978,245, filed Nov. 18, 1992 and entitled "Multi-Dimensional Signal Processing and Display", now U.S. Pat. No. 5,245,587 which is a continuation-in-part of U.S. Ser. No. 07/628,337, filed Dec. 14, 1990 and entitled "Multi-Dimensional Data Processing and Display", now U.S. Pat. No. 5,175,710 which applications are hereby incorporated by reference.

The invention relates in general to electrocardiography, and more particularly to a near real-time processing system to analyze electrocardiographic signals.

Irregular heartbeats, or ventricular arrythmias associated with ischemia and myocardial infarction may result in more serious conditions, and which may lead to sudden cardiac death. Inefficient electrical conduction within the heart issue, such as that due to insufficient blood flow into the heart tissue (ischemia) or to damaged tissue (myocardial infarction) may produce reentrant (wrong-way) electrical conduction within the heart, resulting in preventricular contractions (PVCs), ventricular tachycardia (VT), the rapid, non-sinus origin of heartbeat contractions, and ultimately to ventricular fibrillation (VF), an often fatal condition.

Researchers in the field have discovered several potential diagnostic indicators of patients susceptible to ventricular tachycardia. One of these indicators is referred to as electrical alternans (A/Ns), an alternation between heartbeats. Electrical alternans appear when a normal heartbeat pattern changes every other heartbeat. Changes often occur in the QRS-complex and the ST-segments. Alternating heartbeats may arise from delayed conduction through ischemic tissue. A prolonged delay and recovery period of damaged myocardial tissue results when the damaged tissue is only able to recover and respond every other beat. These delayed conduction paths may give rise to PVCs, VT and VF.

Another potential indicator of patients susceptible to ventricular tachycardia is referred to as ventricular late potentials (VLPs), which are the presence of delayed electrical potentials late in the QRS-complex and the beginning of the ST-segment. Reentrant electrical signals in the general region of the infarct (damaged tissue) may cause delayed electrical potentials, which may lead to irregular, preventricular contractions (PVCs) of tissue which has been isolated from normal electrical conduction pathways.

While electrical alternans and ventricular late potentials appear to be useful diagnostic indicators of patients with susceptibility to ventricular tachycardia, these indicators are not easy to identify through normal ECG analysis. The effected areas of the heart may be relatively small and localized. The associated electrical signals may be relatively weak, compared to the other, more prominent heart characteristics.

Ventricular late potentials may appear as a small "tail," of low frequency energy (~40 Hz) following the predominant QRS-signature. The VLPs are usually so small that they are indistinguishable from normal heartbeat patterns, interference, random noise and other electrical disturbances. Furthermore, respiration and other physical movement may further obscure these weak signals. In some instances these complicating factors may even appear to have similar characteristics as A/Ns and VLPs.

The conventional approach to detecting A/Ns and VLPs is to acquire large amounts of ECG data, under near-ideal conditions, in order to minimize the effects of interference and noise. Subsequent to data analysis, various forms of signal averaging of the ECG waveforms are used to improve the signal-to-noise ratio (SNR) of signals of interest. Unfortunately, not all noise is random and signal averaging tends to increase the SNR of non-random, signal-like noise as well as weak signals of interest.

In detecting electrical alternans, some prior art systems rely on a form of spectral averaging. Data from a patient's ECG leads are used to collect a large number of "normal" heartbeats, which are carefully aligned so that segments of the individual waveforms line up together. Next, for each of a number of small time intervals (i.e. as short as a millisecond in duration) within the QRS-complex and ST-segments, the data is processed longitudinally (i.e. downward, across adjacent heartbeats) to look for the presence of alternating wave structures associated with electrical alternans. Each of these longitudinal data segments is processed using the Fast Fourier Transform (FFT), or other frequency analysis. The resulting frequency spectra are then combined together, using spectral averaging techniques. Using this approach, electrical alternans would appear as frequency energy at the nyquist frequency (i.e. every other heartbeat). In addition to combining data, spectral averaging is intended to reduce noise within the frequency spectra.

In detecting ventricular late potentials, prior art systems also use another form of post-collection signal averaging. Each of a patients X-, Y- and Z-leads are processed to collect and isolate a large number (e.g. several hundred) "normal" heartbeats, which are then aligned, filtered, averaged, squared and added together to produce a single, composite waveform. This signal-averaged waveform is then analyzed in greater detail to look for low-frequency energy (e.g. 40 Hz) at the tail of the QRS-complex and into the beginning of the ST-segment. Multiple, overlapping segments of the composite waveform (e.g. a number of milliseconds in duration) are analyzed, typically using the FFT. The resulting, short-term frequency spectra are combined into a spectrogram display (i.e. frequency by time), which characterizes the temporal evolution of frequency energy through the QRS-complex and into the ST-segment of the heartbeat. Spectral energy at or around 40 Hz may be associated with VLP activity.

While these above forms of signal averaging are commonly used for the detection of alternans and ventricular late potentials, there are several drawbacks. Because of the presence of noise, a large number of waveforms need to be collected and averaged together to increase the signal-to-noise ratio of signal components of interest. Often, special X-, Y- and Z-leads and special medical protocols, or procedures, need to be performed, and the data must be collected and analyzed "off-line" in a post-collection phase. Averaging and/or squaring the waveforms or frequency spectra frequently causes important information about the structure and/or location of the aberrant signal components to be lost.

One prior art system, described in U.S. Pat. No. 4,422,459, is used to detect ventricular late potentials. As proposed, the system must collect and arrange between 200 and 500 heartbeats. Once collected and stored, the prior art system then utilizes a squaring algorithm to combine multiple ECG-leads. While this process may increase the signal-to-noise ratio and enhance signals components of interest, the requisite squaring function eliminates information about the source or location of the signal. Thus, if ventricular late potentials are found, further medical protocols such as Electrophysiology or Echocardiography are required to localize the site of the infarction (i.e. damaged tissue).

Signal averaging is used to reduce the effect of random noise, however, noisy data not only include random, noise-like components, but may also contain non-random, signal-like components such as the predominant QRS-complex, or AC interference (e.g. 60 Hz energy and its higher-frequency harmonics). Signal averaging does not reduce or eliminate these non-random, signal-like noise components and in fact, these unwanted components may obscure and interfere with the recognition of weak VLPs.

Other sources of interference may further obscure the weak, 40 Hz signal common to VLPs. Some of these interfering signals have essentially the same characteristics as late potentials. For example, a 40 Hz "capstan wobble," associated with the recording mechanism in Holter monitors, has been isolated. If not correctly identified as such, this 40 Hz wobble could result in misleading diagnosis.

It is therefore an object of the present invention to provide an electrocardiographic analysis system that will process large amounts of electrocardiographic (ECG) data in near real-time, i.e. as the data is being collected, and enhance weak signals, such as electrical alternans and ventricular late potentials.

It is a further object of the present invention to provide an electrocardiographic analysis system that will isolate and eliminate sources of interference and noise in ECG data.

It is an additional object of the present invention to provide an electrocardiographic analysis system that will reduce, or otherwise suppress the predominant features of the QRS-signal which may interfere with the recognition of weaker components in the late QRS-complex and ST-segments.

It is also an object of the present invention to provide an electrocardiographic analysis system to process ECG data which does not require special X-, Y- and Z-leads, but may be used with other, multiple-lead ECG systems (e.g. 12-leads).

It is a further object of the present invention to provide an electrocardiographic analysis system to isolate key signal patterns, analyze the patterns using high-resolution spectral techniques, and display these key patterns using spectrogram images, or other forms of spectral-temporal displays.

It is also an object of the present invention to provide an electrocardiographic analysis system to process ECG data using smaller data samples, yet with higher precision, than is required using current systems.

It is also an object of the present invention to provide an electrocardiographic analysis system that will project analytical results back into the original sample space (i.e. heartbeat history by waveform), thus permitting the diagnostician to view the full spatial, temporal and waveform structure of features of interest.

Yet another object of this invention is to provide a multi-dimensional ECG processing system that compresses ECG data for further processing and for transmission to a remote location and reconstitution of the received data to accurately represent the original data.

It is also an object of the present invention to enhance and store ECG data in a compressed form, and then rapidly retrieve and display the data from multiple perspectives, such as isolated waveform features, waveform histories, spatial displays, and/or other "slices" through the three-dimensional data cube display of cardiac data. In addition, it is an object of this invention to display the cardiac data as a movie replay of ECG features moving within a three-dimensional, transparent data cube.

SUMMARY OF THE INVENTION

In the preferred embodiment, the multidimensional ECG processing and display system of the present invention is used with an electrocardiographic (ECG) monitoring system. The ECG system provides input ECG data, usually the amplitude of the sensed signal, at multiple, sequential time intervals (e.g. milliseconds), to the processing system. As the data is collected, it is arranged into a three-dimensional matrix, the dimensions being ECG-lead, time history and waveform segment.

The input data (or raw data) is scaled to accentuate or suppress certain leads, time histories and/or waveform segments or portions thereof. The three-dimensional matrix is separated into a number of matrices of two-dimensional data which are concatenated together along the waveform dimension (or other common dimension) to form one large two-dimensional matrix.

The present invention creates and maintains a historic database which is also concatenated with the two-dimensional matrix. This database allows interfering signals and noise to be diminished and other signal components of interest to be enhanced.

Once the data is in the form of a two-dimensional matrix, the data is analyzed efficiently using singular value decomposition (SVD). The two-dimensional concatenated matrix is decomposed to obtain a compressed and enhanced form of the matrix. In the preferred embodiment, singular values and singular vectors are obtained. Singular vectors are partitioned into one or more groups on the basis of their corresponding singular values.

One or more groups of the singular vectors are analyzed further to identify signal components of interest. Selected singular vectors are transformed into their frequency domain representations by the Fast Fourier Transform (FFT), or related techniques. In a similar manner, singular vectors may be adaptively filtered to enhance and display signal components of interest.

Certain data elements in the two-dimensional matrix are enhanced or diminished by modifying the singular values within each of the groups of singular vectors to enhance certain objects that are associated with the ECG data and to diminish other features within the data.

An enhanced two-dimensional concatenated matrix is generated by multiplying together the diagonal matrix of modified singular values and singular vector matrices. The enhanced two-dimensional matrix has enhanced or diminished data values associated with certain signal components.

After data enhancement, the two-dimensional enhanced matrix is partitioned into a series of two-dimensional matrices which are then rearranged to form an enhanced three-dimensional matrix. All or portions of the enhanced three-dimensional matrix can then be displayed. In the preferred embodiment, signal components are displayed as slices through a three-dimensional opaque data cube. Colors or other enhancements are used to display selected characteristics of the signal components. Characteristics may also be displayed as opaque objects within a three-dimensional transparent cube.

BRIEF OVERVIEW OF THE DRAWINGS

Other objects, features, and advantages of the invention will become apparent from the description of a particular embodiment, taken in combination with the drawings, in which:

FIG. 3 is the ECG data of FIG. 2 in matrix form;

FIG. 4 is a Singular Value Decomposition of the ECG data in FIG. 3;

FIG. 19 is the ECG data matrix of FIG. 3, as enhanced according to the present invention;

DETAILED DESCRIPTION OF A PREFERRED EMBODIMENT

The electrocardiographic system of the present invention operates in near "real-time." The present system processes input data in near real-time, as it is collected, with a slight time delay, and reduces or eliminates unwanted data, such as dominant ECG features, effects of respiration, AC interference and background noise. Using the present invention, a medical diagnostician can focus in on features of interest, such as electrical alternans or ventricular late potentials. Electrical alternans are low amplitude signals that are often obscured by respiration artifacts, AC interference and noise. Ventricular late potentials are low amplitude signals that would otherwise be obscured by the QRS-signal complex.

Figure 1:
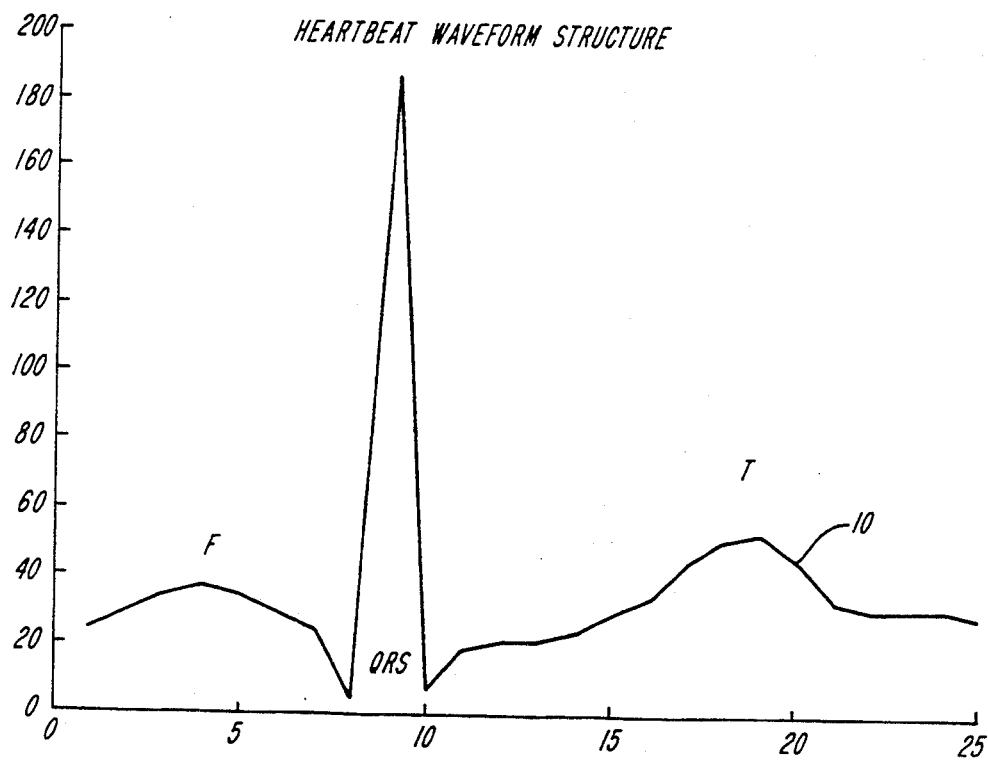
FIG. 1 shows the waveform structure of a typical heartbeat.

FIG. 1 shows ECG cardiac data 10 for a typical heartbeat. The ECG data was received from one lead of an ECG monitoring system. The heartbeat is generally divided into a number of segments, including the P-wave, QRS-complex and T-wave segments.

Figure 2:
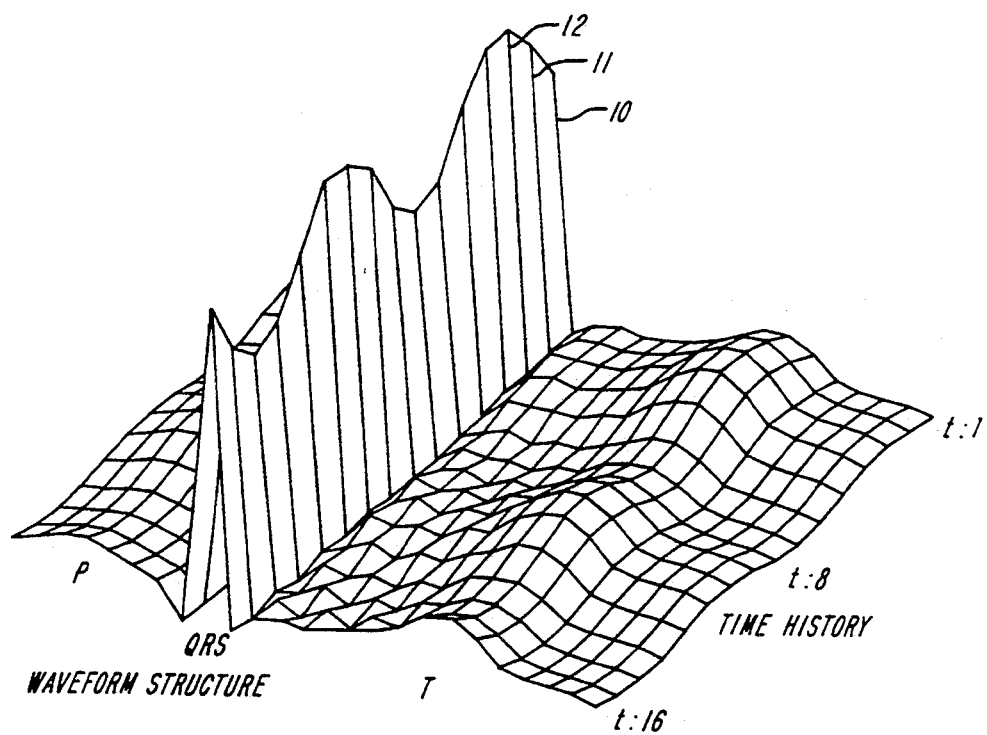
FIG. 2 is a contour graph showing ECG data for multiple heartbeats from a single ECG lead.

Referring to FIG. 2, several heartbeats are arranged in the form of a contour graph. The Y axis shows the heartbeat time history, from heartbeat t:1 to heartbeat t:16. The waveform structure of each heartbeat is displayed along the X axis. The amplitude of each heartbeat is shown by the height of each line. The temporal undulations that are superimposed over multiple heartbeats are caused by the effect of the subject's respiration on the ECG data.

Referring to FIG. 3, the ECG data shown in FIG. 2 is represented in two-dimensional matrix 30. Each row in the matrix corresponds to an individual heartbeat. The values in each row range from 0 to 255 and represent the amplitude of the ECG data signals. In the preferred embodiment, however, the data has a greater range in values, from $-1023$ to $+1023$.

Once the ECG data is placed in matrix form, matrix analysis is then used to describe patterns found in the ECG data. In the preferred embodiment, the ECG data is treated as a matrix, and Singular Value Decomposition is used to decompose the matrix into its temporal variability and waveform structures.

Matrix analysis using singular values and singular vectors is well known in the prior art. The following publications describe such matrix analysis in detail: *Digital Spectral Analysis with Applications,* S. L. Marple, 1987; Matrix Computations, G. H. Golub and C. F. Van Loan, 1989; "Singular Value Decomposition and Least Squares Solutions," *Numerical Math,* G. H. Golub and C. Reisch, 1970; *LINPAC User's Guide,* J. J. Dongerra, et. al., 1979; and "An Improved Algorithm for Computing Singular Value Decomposition," T. F. Chan, *Communications of the ACM,* 1982.

Figure 4:
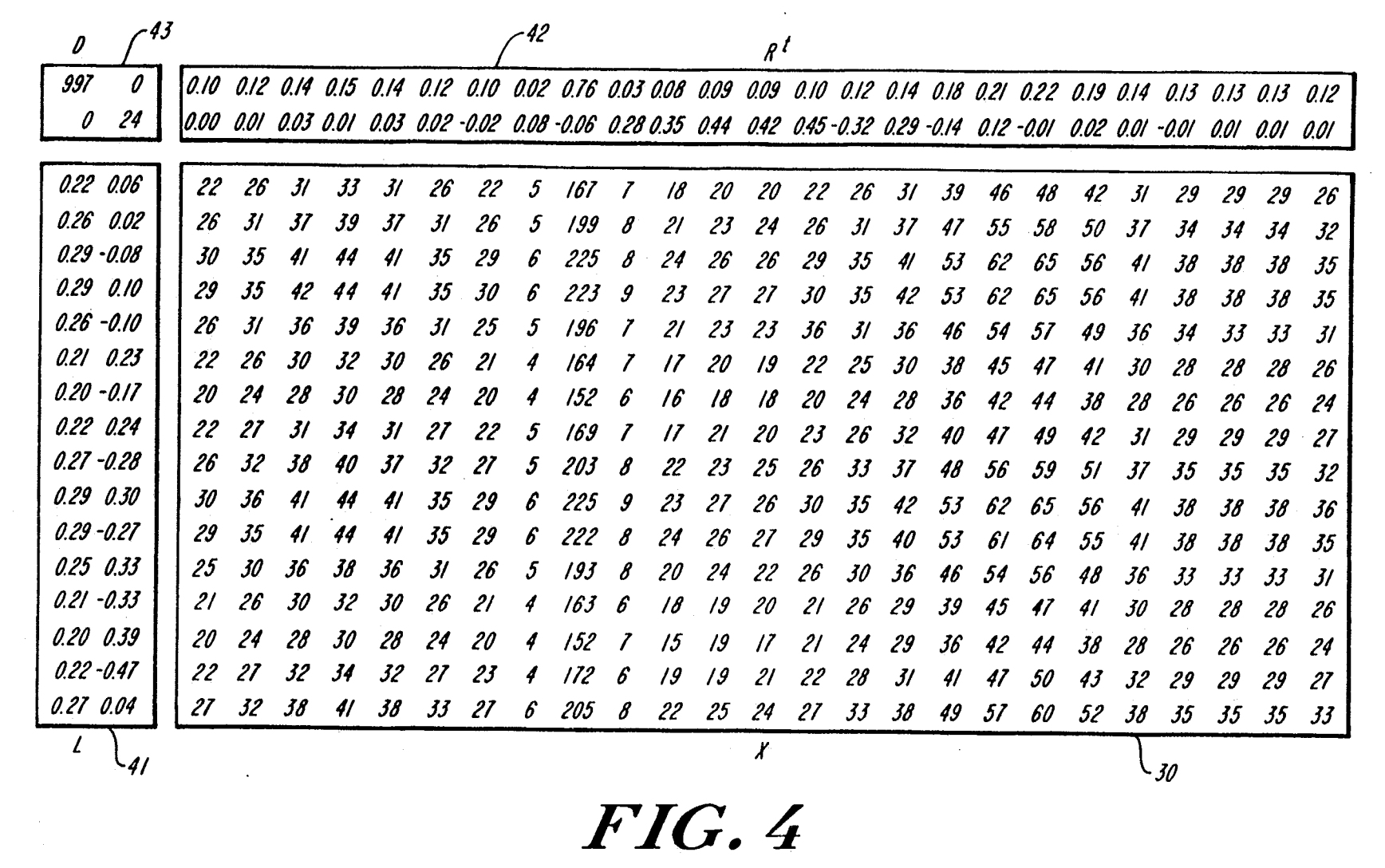

Referring to FIG. 4, the ECG data is represented in a matrix X 30 containing elements arranged in a two-dimensional format with each row corresponding to a single heartbeat and the elements in each row corresponding to the amplitude of the ECG signals in different portions of the waveform. This matrix is decomposed, as described in the above references, into left singular vectors, right singular vectors, and singular values. The left singular vectors are arranged in the columns of L 41 and describe ECG features in terms of their temporal (heartbeat) history. The right singular vectors are arranged in the rows of the matrix $R^t$ 42 and describe ECG features in terms of their waveform structure. The singular values are arranged along the principal diagonal in a matrix D 43 and describe the magnitude of the associated features.

Information in the matrix X 30, which contains input ECG data, is represented by its singular vectors L 41 and $R^t$ 42 and its singular values D 43. The raw data is thus represented in a substantially compressed form. For example, in the above example, the data matrix X 30 contains 16 rows (i.e. 16 heartbeats) of 25 data points each (i.e. 25 samples per beat), for a total of 400 data elements. Through singular value decomposition, these data are closely approximated by a small set of singular values in D, and singular vectors, L and $R^t$, for a data compression of almost 80%. In a full, high resolution EKG system involving 12-leads, the compression obtained may exceed 97%, and the resulting overall computational savings of subsequent A/N and VLP analyses may exceed 90% over existing systems.

The singular values and/or singular vectors are used by the near real-time, multi-dimensional processing system of the present invention to compress, enhance and suppress selected features within the ECG data. The singular values D 43 are displayed in a diagonal form and represent weights used to adjust the singular vectors. The left singular vectors L 41, in the preferred embodiment, correspond to the temporal history, or sequence of heartbeat features within the ECG data and are used for the analysis of alternans. The right singular vectors $R^t$ 42 correspond to ECG waveform structure and are used for the analysis of ventricular late potentials.

The left singular vectors L, right singular vectors $R^t$ and singular values D are used to represent important features within the input data, but in a substantially compressed form. This allows the data to be enhanced, further processed for A/Ns and VLPs, and displayed, without losing any necessary data, but saving substantial amounts of time and computing resources.

In the preferred embodiment of the present invention, the data processing system uses singular value decomposition to describe patterns, remove unwanted components, and isolate and analyze components of interest in ECG data. In alternate embodiments, eigenvector decomposition of the cross-product matrix of the ECG data may be used to decompose the ECG data. The cross-product of the data matrix X is either $X^tX$ or $XX^t$ where $X^t$ represents the transpose of the matrix X. Eigenvector decomposition is also well known in the prior art.

Figure 5A:
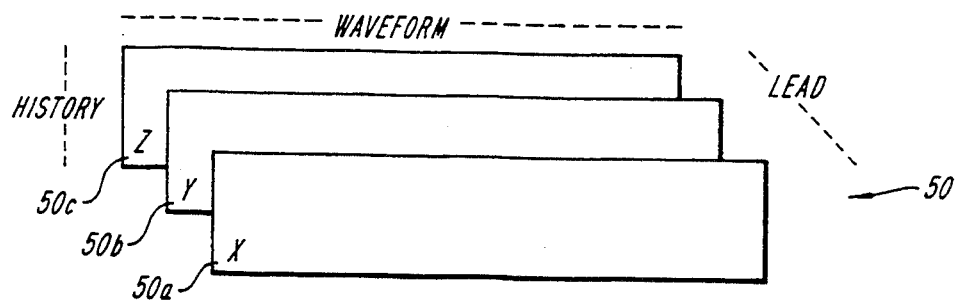
FIG. 5a is three-dimensional data as derived from a 3-lead ECG monitoring system.
Figure 5B:
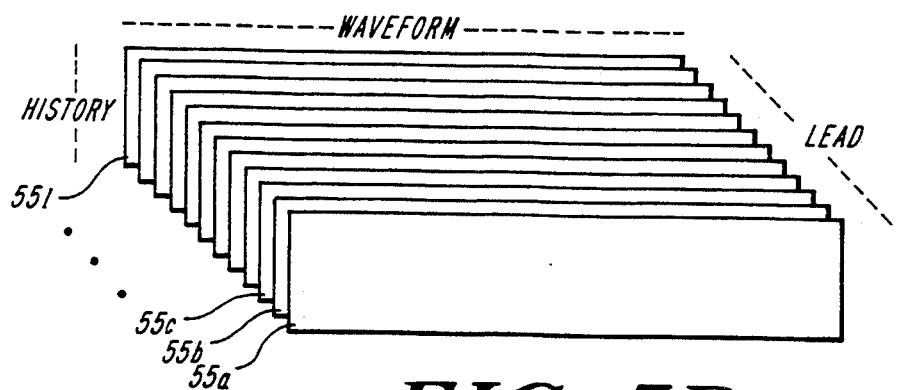
FIG. 5b is three-dimensional data as derived from a 12-lead ECG monitoring system.

Referring to FIGS. 5a and 5b, the present invention stores data from multiple ECG leads in a three-dimensional matrix. Each ECG lead creates one two-dimensional ECG matrix, with the dimensions being time history by waveform structure. In the preferred embodiment, the time history represents less than 15 seconds of data, although in other embodiments, the time interval may be shorter or longer. Prior art systems often require considerably longer time for data collection, followed by numerical analysis at a later time. As shown in FIGS. 5a and 5b, in the present invention, the two-dimensional matrices are stacked side-by-side, creating a three-dimensional ECG "data cube." The dimensions of the three-dimensional data cube are heartbeat time history by waveform structure by ECG-lead.

The amplitude of the signal at a given time, lead and heartbeat is determined by reading the value stored in the ECG data cube at the given time history, waveform segment and ECG-lead. The ECG data cube 50 shown in FIG. 5a contains data from three orthogonal X- 50a, Y-50b and Z-leads 50c. In an alternative embodiment, as shown in FIG. 5b, the ECG data cube 55 is comprised of data obtained from 12 ECG-leads, 55a to 55l and in other embodiments, may contain data obtained from one or any other numbers of leads.

Figure 6:
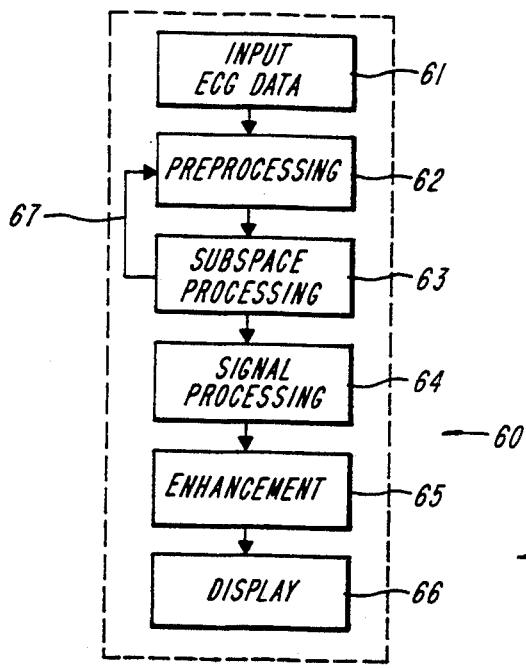
FIG. 6 is a flow chart for the main algorithm of the preferred embodiment of the present invention.

Referring to FIG. 6, a flow chart for the main algorithm 60 of the present invention is shown. The algorithm operates on three-dimensional ECG input data 61. Initially, three-dimensional ECG input data 61 (as shown in FIG. 5) is obtained, weighted and reformatted into one or more two-dimensional matrices by a Preprocessing Function 62. The Subspace Processing Function 63 compresses the ECG data by decomposing the two-dimensional data matrix into its singular values and singular vectors. The Subspace Processing Function then enhances the compressed data by modifying or eliminating some of the singular vectors. Prominent features, interference and noise are suppressed and/or eliminated from the data. The Subspace Processing Function allows Signal Processing Functions to operate on compressed and enhanced ECG data, rather than the original data. This results in a substantial reduction in the overall processing load of the Signal Processing stage.

The resulting compressed and enhanced left and right singular vectors L, $R^t$, are passed from the Subspace Processing Function 63 to the Signal Processing Function 64 for analysis of electrical alternans and ventricular late potentials. The Enchancement Function 65 expands the resulting selected data into an enhanced, three-dimensional form, which is then displayed by the Display Function 66.

As the ECG data is passed in a forward direction through these functions, history data 67 is also passed backwards from the Subspace Processing Function 63 to the Preprocessing Function 62 to assist in enhancement and monitoring features of interest. History data consists of a special set of waveform structures of features of interest, such as prospective electrical alternans components and ventricular late potentials within the ECG data. The waveform structures of the history data are in the form of right singular vectors which are associated with features of interest $R^t_{fi}$ and with features not of interest $R^t_{fn}$. In addition, some of the features of interest $R^t_{fi}$ have been weighted or otherwise modified (e.g. by a function of their corresponding singular values or singular vectors) to form weighted features of interest $R^t_{wfi}$. In alternative embodiments, the left singular vectors are similarly modified.

History data of features of interest $R^t_{fi}$ are calculated by the Subspace Processing Function 63 and are passed back to the Preprocessing Function 62 to be concatenated with new ECG data. The purpose of this feedback is to enable the energy from weak features of interest to build up to the point where the features of interest may be distinguished from background noise.

Weighted history data for features of interest $R^t_{wfi}$ are also passed forward from the Subspace Processing Function 63 to the Signal Processing Function 64 for analysis of electrical alternans and ventricular late potentials.

Figure 7:
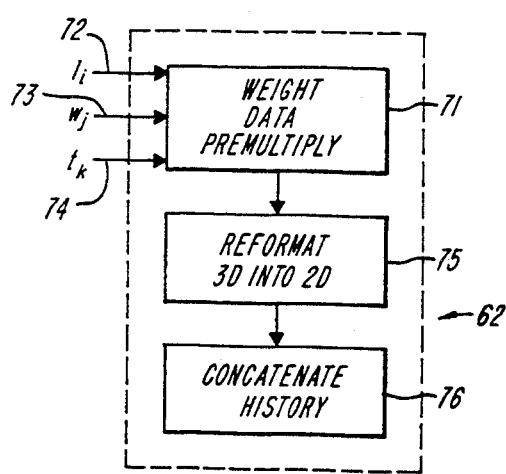
FIG. 7 is a flow chart of the Preprocessing Function.

The history data of features not of interest $R^t_{fn}$ are also calculated by the Subspace Processing Function 63 and are fed back to the Preprocessing Function 62 and forward to the Signal Processing Function 64. This information is used to set parameters for further analysis or enhancement and in alternative embodiments may be used to show respiration effects and other features in the data without obscuring features of interest, or to reconstruct the original data. cl The Preprocessing Function FIG. 7 shows the Preprocessing Function 62 in greater detail. The Preprocessing Function weights the input data at 71 to accentuate or suppress certain leads, waveform segments and/or time intervals. Each ECG lead has an associated coefficient $l_i$ 72, which is used to appropriately scale the data on specified leads. Each segment of a waveform has a coefficient $w_j$ 73, which is used to scale the data within each heartbeat segment. Similarly, each heartbeat has an associated temporal coefficient $t_k$ 74, which is used to scale the data within particular heartbeats.

Increasing the magnitude of data at selected ECG leads, waveform segments and time histories increases the importance of the associated data in subsequent analyses. Decreasing the magnitude of data at other selected ECG leads, waveform segments and time histories similarly decreases the importance of the associated data in subsequent analyses. The ECG lead, waveform and time coefficients can either be preset, set by an automatic function, or interactively altered by an operator.

In the preferred embodiment of the present invention, the input data may also be premultiplied by selected singular vectors. The left singular vectors for features not of interest $L_{fn}$ and right singular vectors for features not of interest $R^t_{fn}$ may be used to remove selected features not of interest. For example, new ECG data $X_{t:1}$ may be premultiplied by $L^t_{fn}$ to obtain an update of $R^t_{fn}$, then expanded by premultiplying the results by $L_{fn}$ and subtracted from $X_{t:1}$, i.e.

$$Xr_{t:1} = X_{t:1} - L_{fn}(L^t_{fn} X_{t:1}),$$

or
alternatively, through mathematical identities, $$Xr_{t:1} = (I - L_{fn} L^t_{fn}) X_{t:1},$$

where I is the identity matrix. However, in other embodiments, it may be computationally more efficient to enhance input data by postmultiplying the input data by previously determined right singular vectors $R^t_{fn}$, i.e.:

$$Xr_{t:1} = Xr_{t:1} - (Xr_{t:1} R_{fn}) R^t_{fn},$$

or $$Xr_{t:1} = Xr_{t:1}(I - R_{fn} R^t_{fn}).$$

In this manner, features not of interest may be removed from the input data in the Preprocessing Function.

The input data is then reformatted from a series of two-dimensional matrices (or a three-dimensional data cube) into one concatenated two-dimensional matrix (shown at 75). The two-dimensional concatenated matrix is concatenated with history data at 76.

Subspace Processing Function

Figure 8:
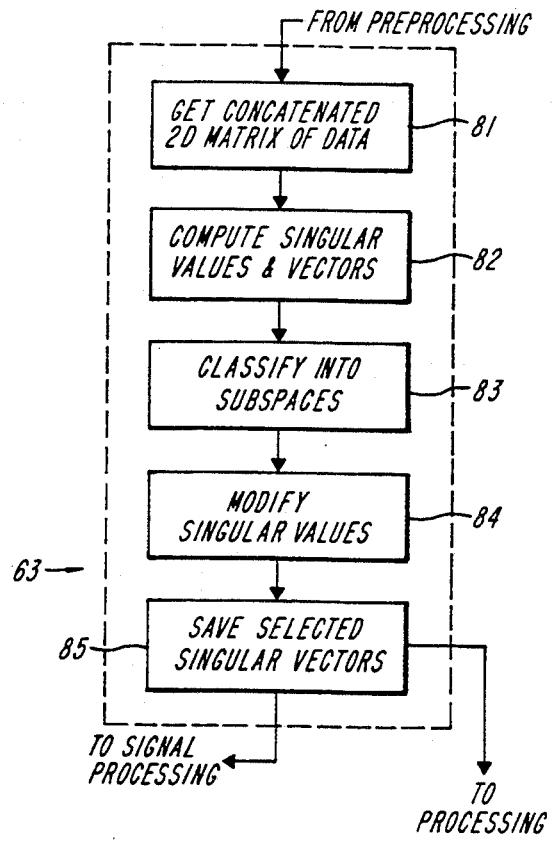
FIG. 8 is a flow chart for the Subspace Processing Function.

Referring to FIG. 8, the Subspace Processing Function 63 is shown in greater detail. The Subspace Processing Function compresses and enhances the two-dimensional ECG data, analyzes the data in terms of its dominant singular values and associated left and right singular vectors, and partitions the data into subspaces on the basis of their singular values, singular vectors, or other criteria. Then selected singular vectors are passed on to the Signal Processing Function for further analysis. Selected singular vectors are also passed back to the Preprocessing Function to enhance or diminish data features in subsequent analyses.

Figure 9:
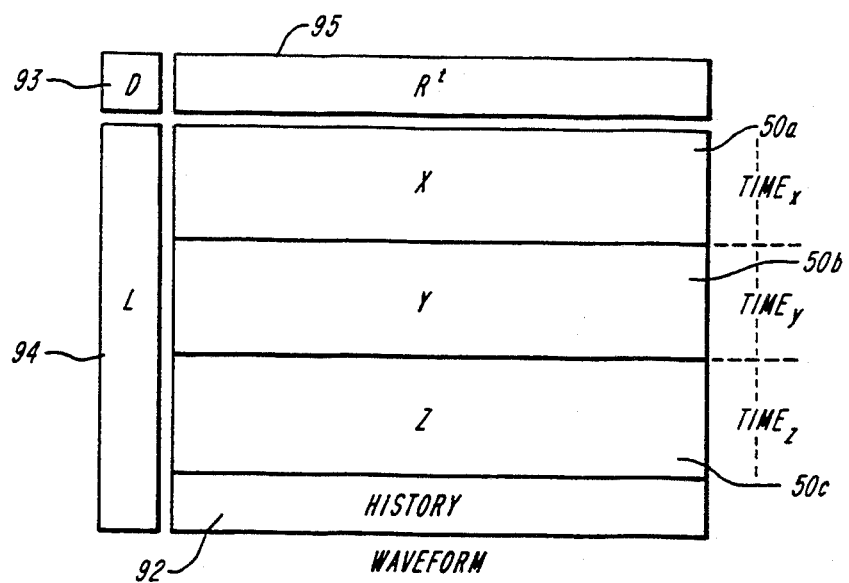
FIG. 9 is the ECG data as decomposed using the preferred method into a compressed and enhanced form.

The two-dimensional data is obtained from the Preprocessing Function (shown at 81) and is analyzed (shown at 82). Subsets are selected for a compressed and enhanced form (shown at 83 and 84) by the Subspace Processing Function. There are several ways the three-dimensional data may be compressed and enhanced. Referring to FIG. 9, the preferred method to decompose the three-dimensional data into a compressed and enhanced form is shown. The series of two-dimensional matrices, or the three-dimensional data cube (as shown in FIG. 5a) is arranged as a number of two-dimensional matrices. Each matrix has dimensions time history vs. heartbeat waveform structure for one lead. The two-dimensional matrices are then concatenated along a common dimension. In the preferred embodiment, the two-dimensional matrices are concatenated along the waveform dimension, resulting in one concatenated two-dimensional matrix. The resulting matrix 91 has heartbeat waveform structure in one dimension and a combination of time history and lead in the other dimension. Compressed and enhanced waveform history data 92 from previous analyses are concatenated along the bottom of the matrix. The concatenated two-dimensional matrix is decomposed into its singular values D 93, left singular vectors L 94 and right singular vectors $R^t$ 95. In alternative embodiments, the matrices may be concatenated along the time history dimension, or the ECG-lead dimension.

Figure 10:
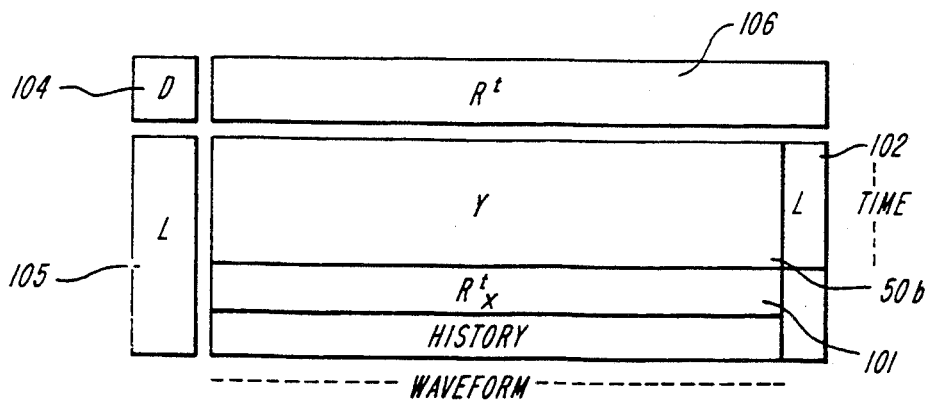
FIG. 10 is the ECG data as decomposed using a first alternative method into a compressed and enhanced form.

Referring to FIG. 10, a first alternative method to decompose the three-dimensional matrix into a compressed and enhanced form is shown. In this method, data for each lead is decomposed into its singular values and singular vectors, subsets of which are then concatenated with the next lead. For each lead, data is formatted into a two-dimensional matrix having dimensions time history versus waveform structure. As each ECG lead is processed, the singular vectors, which represents results from prior ECG analyses, are appended to both the right and bottom edges of the matrix. History data in the form of right singular vectors $R^t$ (from prior analyses) are appended to the bottom of the matrix. This matrix is then decomposed into its singular values, left singular vectors L (representing time history) and right singular vectors $R^t$ (representing waveform structure). These results are then concatenated with data from the next lead. For example, FIG. 10 shows processing ECG data from the Y-lead 50b, while concatenating selected singular vectors $R^t_x$ 101 and $L_x$ 102 from prior analysis of the X-lead. History data 103 is concatenated to the bottom of the matrix, and the matrix is decomposed into its singular valves D 104, left singular vectors L 105 and right singular vectors R 106. A similar series of steps is then repeated for analysis of the Z-lead.

Figure 11:
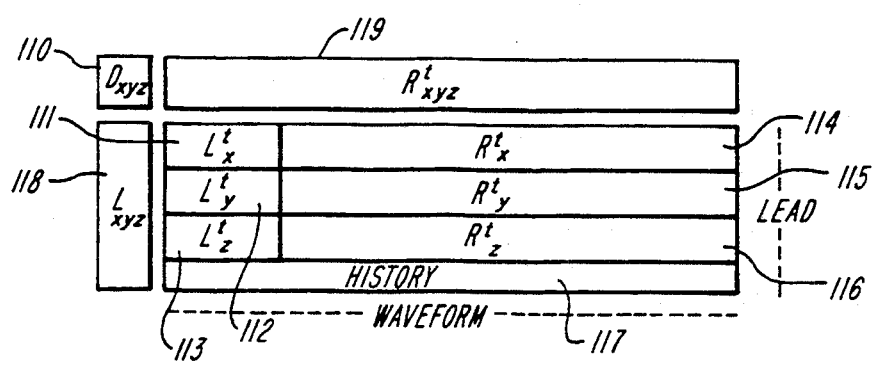
FIG. 11 is the ECG data as decomposed using a second alternative method into a compressed and enhanced form and represents a further compression of the data of FIG. 10.

Referring to FIG. 11, a second alternative method to decompose the three-dimensional data into a compressed and enhanced form is shown. Data from each lead X, Y, and Z is separately decomposed into its singular values $D_x$, $D_y$ and $D_z$, left singular vectors $L_x$, $L_y$ and $L_z$ and right singular vectors $R^t_x$, $R^t_y$ and $R^t_z$. The singular vectors from each of the ECG leads (111, 112, 113, 114, 115, 116) are then concatenated, or "data fused," together to form one matrix. History data 117, in the form of concatenated singular values ($L^t_{xyz}:R^t_{xyz}$), from the prior analyses, are also appended to the matrix. Each row is multiplied by a scale factor (such as the associated singular value or other criteria). Each row entry in this matrix represents both weighted temporal and waveform characteristics of features from each lead. Next, the matrix is analyzed using singular value decomposition into $L_{xyz}$ 118, $D_{xyz}$ 110 and $R^t_{xyz}$ 119. The results represent the multi-lead data fusion and further compression and enhancement of the full, three-dimensional ECG data cube for a specific time interval. The left singular vectors from this analysis $L_{xyz}$ 118 correspond to the X-, Y- and Z-leads, while the right singular vectors represent a combination of time history (former L's) and waveform (former $R^r$s).

Figure 12:
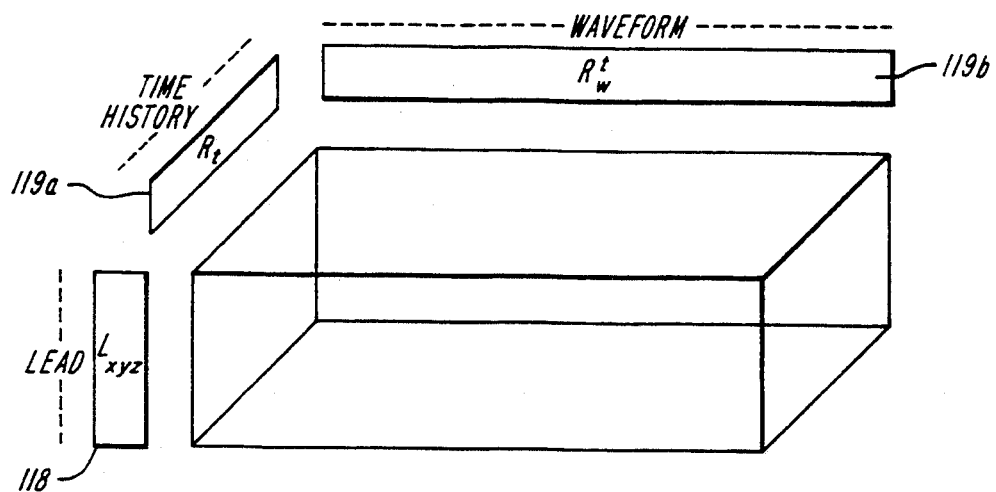
FIG. 12 is another representation of the compressed and enhanced ECG data in FIGS. 10 and 11.

Referring to FIG. 12, the compressed data shown in FIGS. 10 and 11 is represented by the singular vectors $L_{xyz}$ 118 and $R^t_{xyz}$ 119. These singular vectors represent, in compressed form, important characteristics of the entire ECG data cube for a particular time. The ECG lead characteristics are described by the left singular vectors $L_{xyz}$ 118. The time history characteristics are described by $R_t$ 119a, the leftmost portion of the right singular vector $R^t_{xyz}$ 119. The waveform characteristics of the ECG data are described by the $R^t_w$ 119b, rightmost portion of the right singular vectors $R^t_{xyz}$ 119. By multiplying these vectors together, it is possible to accurately recreate an enhanced representation of the full, three-dimensional ECG data cube.

Figure 13:
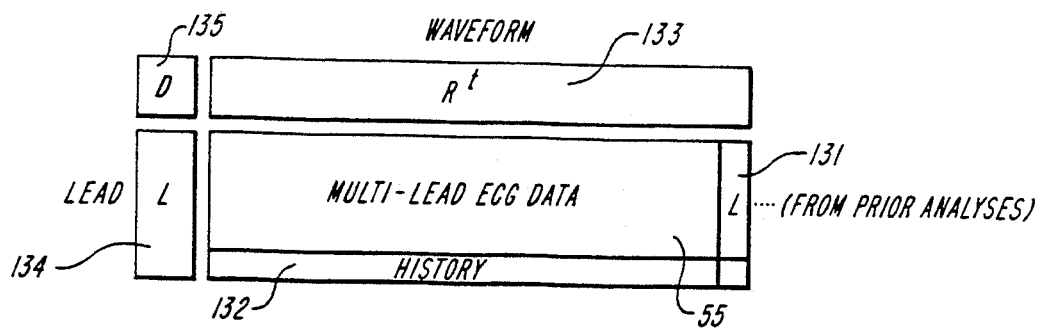
FIG. 13 is the ECG data as decomposed using a third alternative method into a compressed and enhanced form.

Referring to FIG. 13, a third alternative method to decompose the three-dimensional data into a compressed and enhanced form is shown. For each heartbeat time interval, data 55 from the multiple leads (e.g. the 12-lead ECG data shown in FIG. 5b) are arranged in matrix form. This matrix has the dimensions ECG-lead by waveform structure. History data in the form of left singular vectors L 131 and right singular vectors $R^t$ 132 from prior analyses are appended to the right side and bottom of this matrix, respectively. The matrix is then decomposed into its singular values 135 and singular vectors. The resulting right singular vectors $R^t$ 133 represent waveform characteristics of the single heartbeat. The resulting left singular vectors L 134 represent the distribution of these characteristics across the multiple ECG leads and may be used to localize the orientations of electrical conduction of certain features within the ECG data. An advantage of this third alternative embodiment of the present invention is that ECG data is analyzed in real time, i.e. as each heartbeat is acquired. This alternative embodiment differs from other embodiments, which collect a number of heartbeats (e.g. over a period of 15 seconds) prior to analysis.

History Data

In the preferred embodiment, history data is a special set of waveform characteristics in the form of right singular vectors which are associated with features of interest $R^t_{fi}$. In addition, some of the features of interest have been weighted, to form weighted features of interest $R^t_{wfi}$.

History data for waveform features of interest $R^t_{fi}$ are continuously updated by the Subspace Processing Function and are passed back to the Preprocessing Function. The histories of waveform features of interest are in the form of right singular vectors $R^t_{fi}$, which are determined through analysis of the singular values or other criteria in the Subspace Processing Function, or the Signal Processing Function. The history data of the features of interest $R^t_{fi}$ are scaled and concatenated with the weighted ECG data in the two-dimensional data matrix. The entire data set, containing the current input ECG data and historical data, is then analyzed using singular value decomposition. In the preferred embodiment, this process is repeated every time interval, which may represent approximately 15 seconds, although in alternative embodiments, the history data base may represent other time intervals.

Figure 14:
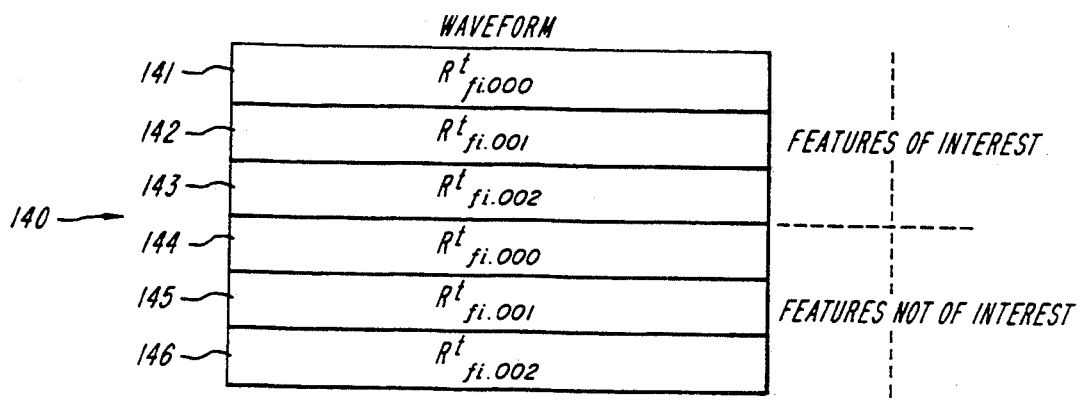
FIG. 14 is the ECG history database for features of interest and features not of interest in the preferred embodiment.

Referring to FIG. 14, the waveform history database of the preferred embodiment is shown. The waveform history database retains waveform histories of features of interest $R^t_{fi}$, and waveform histories of features not of interest $R^t_{fn}$ from various leads. Both features of interest $R^t_{fi}$ and features not of interest $R^t_{fn}$ may be weighted within this data base, resulting in $R^t_{wfn}$ and $R^t_{wfn}$, respectively.

The waveform history database 140 is updated every time interval by storing the most recently received history data of features of interest as $R^t_{fi.000}$ 141 and features not of interest $R^t_{fn.000}$ 144 to represent the recent historical status of the ECG data. Every time interval, the status of the existing history data is updated. Thus, the existing $R^t_{fi.000}$ becomes $R^t_{fi.001}$ and the existing $R^t_{fi.001}$ becomes $R^t_{fi.002}$ and so on to $R^t_{fi.nnn}$ where "nnn" corresponds to the length of the compressed time history.

The waveform history data for features not of interest $R^t_{fn}$ are similarly continually updated by the Subspace Processing Function, and are passed back to be used by the Preprocessing Function. These data are also weighted and concatenated with the two-dimensional weighted ECG data. The waveform history data base is created and continually updated using waveform characteristics received from the Subspace Processing Function. The history database contains historic data that shows the status of the ECG data for several previous time intervals.

The present invention thus creates and maintains waveform historical databases, which are efficiently maintained in compressed and enhanced form, and represent features of the ECG data at various time intervals. Each new analysis includes the compressed and enhanced historical data, which is equivalent to a complete analysis of the full (uncompressed) historical data, yet at a fraction of the computational cost.

In alternative embodiments, history data consisting of time history, ECG-lead and/or waveform structure for features of interest, features not of interest and/or noise may similarly be entered into the historic data base.

Example of Subspace Processing Function

Figure 15:
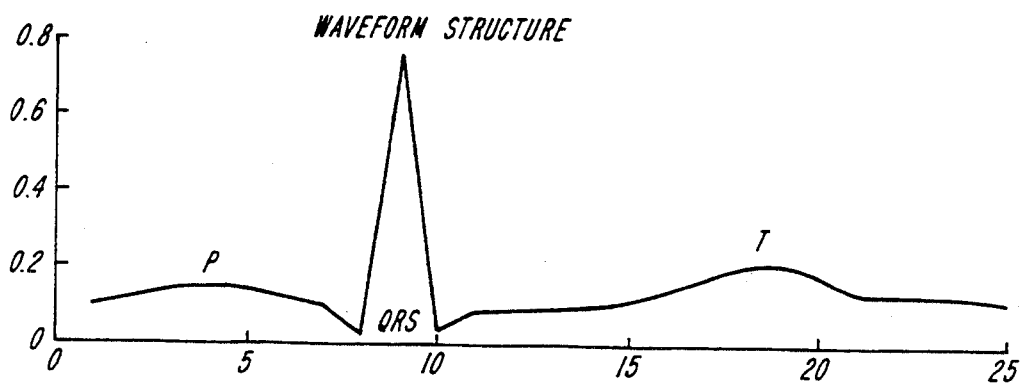
FIG. 15 is a graphic display of the waveform structure of the dominant heartbeat characteristics in the ECG data of FIGS. 2 and 3.

The raw data obtained for sixteen heartbeats from one lead is arranged as data in matrix X in FIG. 4. The matrix X 30 is defined in terms of its singular values D 43, its left singular vectors L 41 and its right singular vectors $R^t$ 42. In the present invention, the left singular vectors are used for analysis of electrical alternans and the right singular vectors are used for analysis of ventricular late potentials. The singular value shown in the first row and first column $d_{1,1}$ of the singular value matrix D, and having the magnitude 997, indicates the magnitude of the corresponding left and right singular vectors shown in the first column of the matrix L and the first row of the matrix $R^t$. As shown in FIG. 15, the right singular vector $r^t_1$ in the first row of $R^t$ indicates the predominant heartbeat structure with the P-wave located at waveform segment 4, the QRS-complex located at waveform segment 9 and the T-wave structure located at waveform segment 19.

Figure 16:
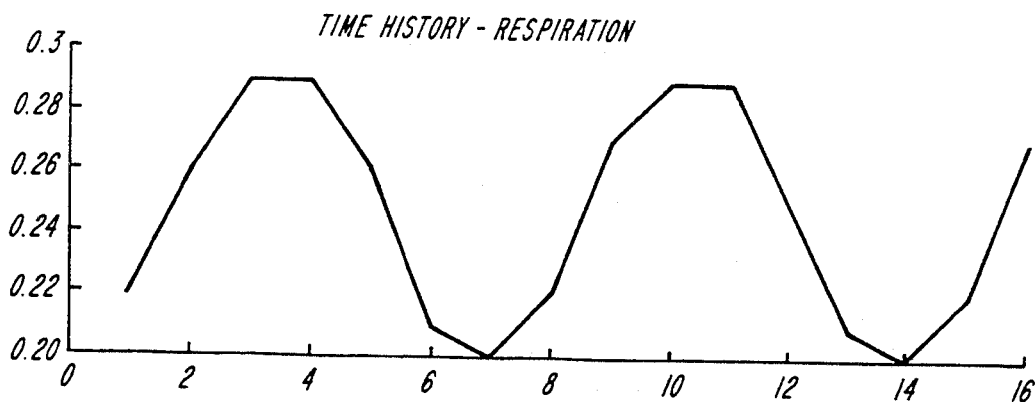
FIG. 16 is a graphic display of the temporal history of the effect of respiration in the ECG data in FIGS. 2 and 3.

Referring to FIG. 16, the associated left singular vector $l_1$ shows the time history of this predominant ECG feature. As may be seen by the slow undulating structure, this component reflects the effect of respiration on the ECG data.

Figure 17:
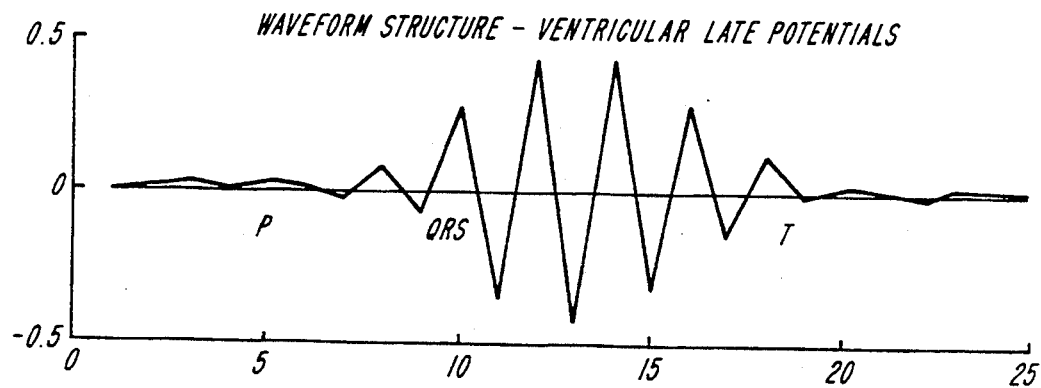
FIG. 17 is a graphic display of the waveform structure of weak ECG characteristics which are associated with the presence of ventricular late potentials in the late QRS-complex and the early ST-segments in the ECG data of FIGS. 2 and 3.
Figure 18:
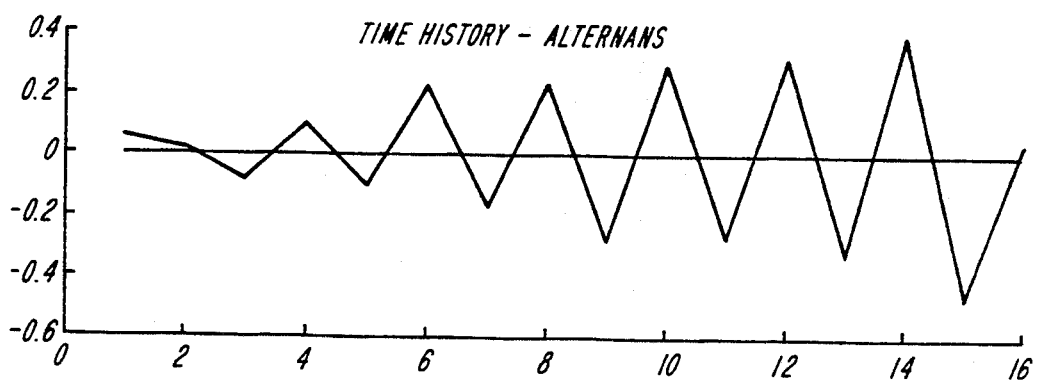
FIG. 18 is a graphic display of the temporal history of electrical alternans in the ECG data of FIGS. 2 and 3.

Referring again to FIG. 4, the singular value at $d_{2,2}$ has a value of 24, indicating the magnitude of another, weaker feature. As shown in FIG. 17, the right singular vector $r^t_2$, the second row of $R^t$ in FIG. 4, indicates a high frequency variation, starting at the end of the QRS-complex at waveform segment 9 and extending into the ST-segment, located between waveform segments 10 and 19 and represents the electrical frequency activity associated with ventricular late potentials. As shown in FIG. 18, the corresponding left singular vector $l_2$, the second column of the matrix L in FIG. 4, shows an alternating increasing and decreasing pattern which increases in magnitude from time:0 to time:16 and represents electrical alternan features.

In the above example, important features have been combined into single pairs of singular vectors. Dominant heartbeat structure and respiration are represented within the first pair of singular vectors $l_1$ and $r^t_1$, while electrical alternans and ventricular late potentials are described by the second pair of singular vectors $l_2$ and $r^t_2$. In other ECG data, such features may appear in separate, distinct singular vectors, or in sets of singular vectors.

Referring again to FIG. 8, after obtaining a combination of concatenated data and compressed history in the form of a two-dimensional matrix, the Subspace Processing Function 63 performs a singular value decomposition of the two-dimensional matrix (shown at 82). Next, the Subspace Processing Function determines a preliminary subspace separation of the results (shown at 83). The singular vectors that have been derived from the input ECG data are classified into subspaces based on the magnitudes of the singular values or by some other criteria. In the preferred embodiment, singular vectors are classified as one of three general categories: features not of interest, including predominant heartbeat characteristics, respiration effects, and effects of AC interference; weak features of interest; and noise. There may be different subspace categories in alternative embodiments. Furthermore, in alternative embodiments, preliminary classification may occur in the Subspace Processing Function, while further, more sophisticated classification may occur in the Signal Processing Function.

Figure 19:
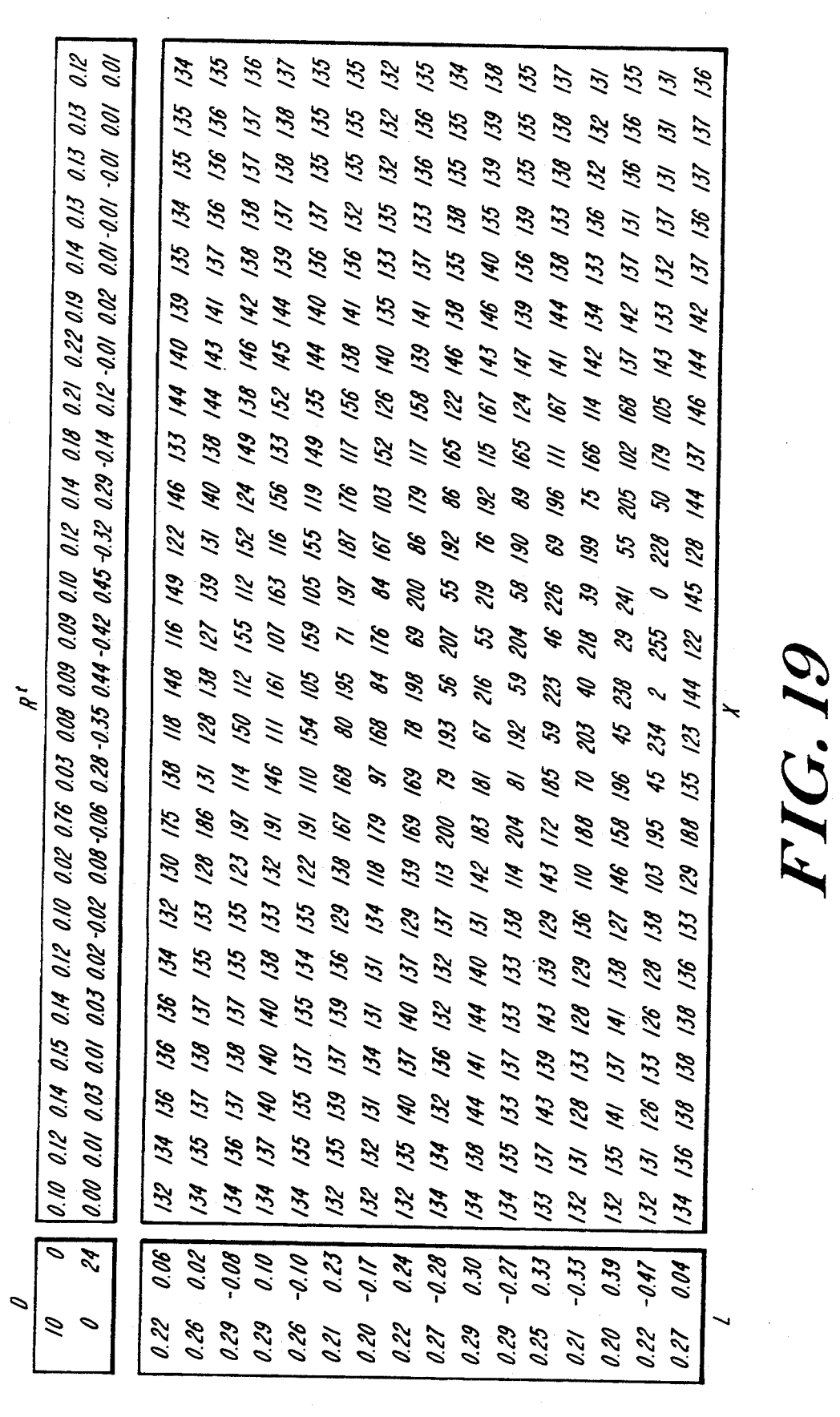

The data is then enhanced at 84 by modifying singular values according to the subspace separation. Singular values corresponding to noise and strong features not of interest are reduced, while the singular values corresponding to features of interest are increased. The data is then expanded back into matrix form to give a full ECG gram display of features of interest. The results of enhancing the ECG data from FIG. 3 is shown in FIG. 19. The values $D_{efi}$ of the data have been modified to diminish strong features and to enhance other features of interest. The singular value associated with the predominant heartbeat structure and respiration, $d_{1,1}$ has been reduced from 997 to 10. The singular value associated with the electrical alternans and ventricular late potentials, $d_{2,2}$ remains at a value of 24. In alternative embodiments some or all singular values may remain as computed, be modified, or set to zero, based on various criteria. Note that the values of the singular vectors in L and $R^t$ remain unchanged. In alternative embodiments, however, these data may be further enhanced or modified.

Figure 20:
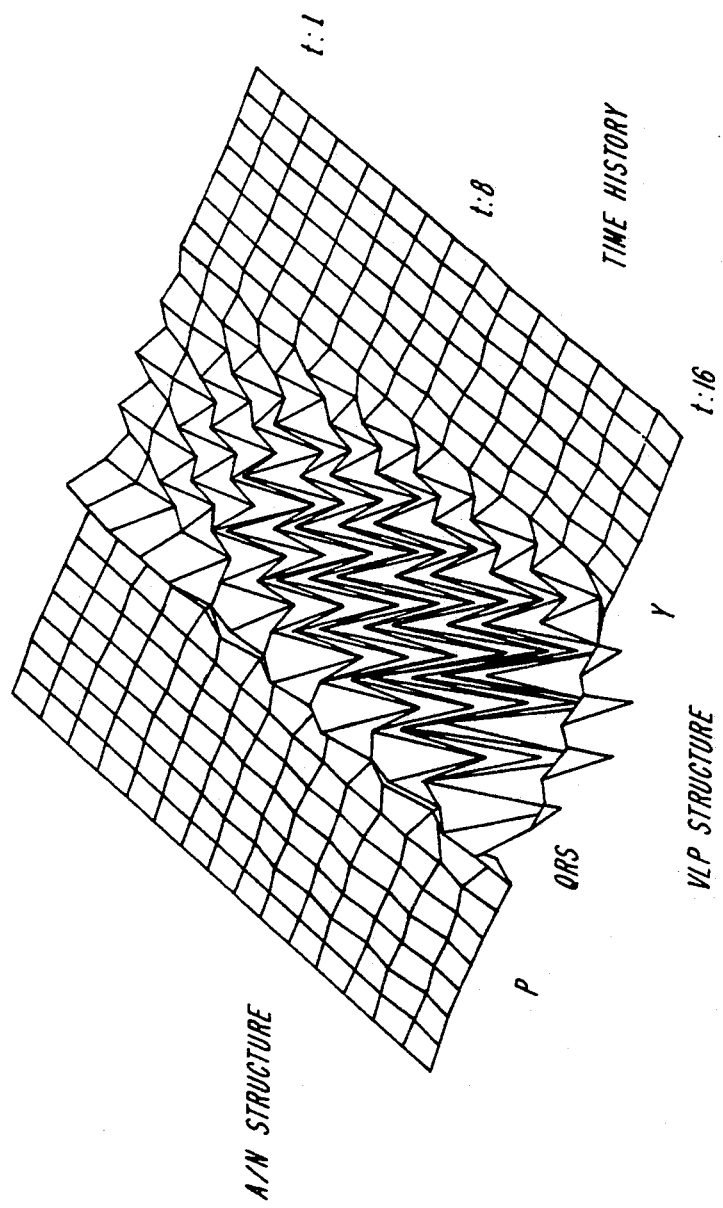
FIG. 20 is a contour graph of the enhanced ECG data in FIG. 19, showing electrical alternans and ventricular late potentials.

FIG. 20 is a contour graph showing ECG features of interest from FIG. 19, when the normal heartbeat structure and respiration effects have been diminished and the electrical alternans and ventricular late potentials have been enhanced.

Referring again to FIG. 8, the Subspace Processing Function 63 computes and saves selected singular vectors. A set of temporal history data $L_{fi}$, which describes temporal characteristics of heartbeat features of interest, is passed on to the Signal Processing Function for further processing and analysis of electrical alternans. A set of associated right singular vectors $R^t_{fi}$, which corresponds to waveform characteristics of features of interest, is passed on to the Signal Processing Function for further processing and analysis of ventricular late potentials. In alternative embodiments of the present invention, certain singular vectors are rotated using varimax rotation, or other criterion, to maximize their loadings to accentuate particular times, ECG-leads or heartbeat structures. These operations are well known in the prior art.

The right singular vectors associates with features of interest $R^t_{fi}$ are weighted by adjusting the singular values, or other criteria, resulting in weighted features of interest $R^t_{wfi}$. The Subspace Processing Function passes waveform structure data in the form of right singular vectors $R^t_{fi}$ back to the Preprocessing Function. The Subspace Processing Function also passes the weighted singular vectors $R^t_{wfi}$ forward to the Signal Processing Function.

Signal Processing Function

The resulting compressed and enhanced data, in the form of singular vectors, are passed on to the Signal Processing Function 64 for further analysis. In the ECG data processing system of the present invention, two forms of advanced signal processing are: (1) spectral processing for analysis of electrical alternans; and (2) spectral-temporal processing for analysis of ventricular late potentials. In alternative embodiments, other forms of diagnostic analyses are performed on the compressed and enhanced data, rather than the original ECG data, generally resulting in higher performance, yet at significant computational savings.

Processing for analysis of electrical alternans is well known in the prior art. In the present invention, however, the input to this processing stage is in the form of left singular vectors L, rather than raw ECG data. The requirement for spectral averaging has been eliminated by the use of singular value decomposition. Furthermore, by diminishing or eliminating certain singular vectors, features not of interest, such as AC interference, may be suppressed or removed, resulting in greater performance.

Figure 21:
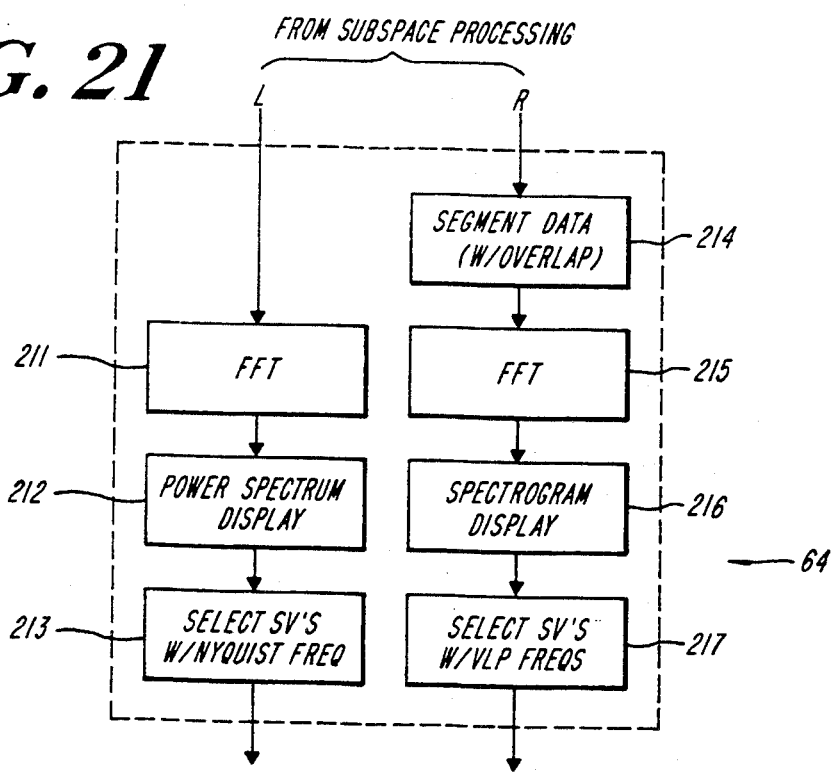
FIG. 21 is a flow chart of the Signal Processing Function.

FIG. 21 shows the Signal Processing Function 64 in greater detail. The left singular vectors L are transformed into the frequency domain using the Fast Fourier Transform (FFT) at 211, or some other comparable frequency transformation process. The resulting power spectra are then examined at 212, either manually, or using an automated process, to determine if there is significant energy at the nyquist frequency (which corresponds to a temporal waveform with every-other heartbeat variations). Alternatively, those singular vectors showing lower frequency energy, such as that due to respiration, are either rejected, or classified into a different subspace. Those singular vectors containing data of interest, such as those having significant nyquist frequency energy, are selected at 213 and passed on for further processing.

Again referring to FIG. 21, the right singular vectors $R^t$ are segmented into a number of time intervals (i.e. offset from each other, yet with a certain degree of overlap between samples), and processed using the FFT at 215, or other form of frequency analysis, to determine their corresponding power spectra. These spectral results may be displayed in the form of a spectrogram image at 216, and examined for the presence of spectral energy at the end of the QRS-complex and into the ST-segment which may be associated with ventricular late potentials (e.g. 40 Hz spectral energy). Those singular vectors with significant energy at 60 Hz, or its harmonics (e.g. 120 Hz, 180 Hz, 360 Hz, etc.), may be classified into a separate subspace associated with AC interference. Those singular values having characteristics of interest, such as 40 Hz energy are selected at 217 and passed on for further processing.

This form of spectral-temporal processing is well known in the prior art. However, in the present invention right singular vectors $R^t$, rather than the raw ECG data, is used for analysis of ventricular late potentials. The requirement for signal averaging has been eliminated by the use of singular value decomposition. In addition, certain features, such as the prominent QRS-complex, may be suppressed by diminishing or eliminating certain singular values, resulting in greater performance.

Enhancement Function

Referring again to FIG. 6, after passing through the Signal Processing Function 64, the compressed ECG data is passed on to the Enhancement Function 65. Presentations of enhanced features of interest $X_{efi}$ are generated by the outer product multiplication of the left singular vectors $L_{fi}$ and the weighted right singular vectors $R^t_{wfi}$, such as shown in FIG. 20. Note that the weighted right singular vector $R^t_{wfi}$ may be weighted by the modified singular values $D_{efi}$ i.e.:

$$R^t_{wfi} = D_{efi} \times R^t_{fi}$$

In a similar manner, enhanced presentations of data features not of interest $X_{efn}$ may be generated by the outer product multiplication of the left singular vectors $L_{fn}$ and the weighted right singular vectors $R^t_{wfn}$:

$$X_{efi} = L_{fi} R^t_{wfi},$$

and $$X_{efn} = L_{fn} R^t_{wfn}.$$

In alternative embodiments, either or both left and right singular vectors may be further enhanced before expansion.

FIG. 20 shows a contour graph of the enhanced ECG data of FIG. 2 for one ECG lead. In this figure, the normal heartbeat structure and respiration effects have been diminished and electrical alternans and ventricular late potentials have been enhanced.

After unwanted features and noise have been suppressed, and features of interest have been enhanced, the enhanced ECG data is again expanded and reformatted into three-dimensional form.

The reverse of the procedure used to compress the data is used to expand the data. In the preferred embodiment, the data is expanded from compressed, two-dimensional form into three-dimensional form by expanding singular vectors to one large two-dimensional matrix and then partitioning the two-dimensional matrix along the common dimension into a series of two-dimensional matrices. The series of two-dimensional matrices are then arranged into a three-dimensional format for display.

In the first and second alternative embodiments, shown in FIGS. 10 and 11, the compressed data (singular vectors $L_{fi}$ and $R^t_{wfi}$) are expanded into a two-dimensional matrix for each ECG-lead. This process continues until data for all of the ECG-leads have been expanded.

In the third alternative embodiment, as shown in FIG. 12, all three compressed and enhanced matrices are multiplied together to obtain a full set of ECG data. For each level n, the matrix $(R_t R^t_w)$ is premultiplied by the appropriate values of $L_{wyx}$ for the n level. The resulting data for individual ECG-leads represent the expanded, enhanced three-dimensional data. In alternative embodiments the matrix $(L_{xyz} R^t_w)$ may be premultiplied by the appropriate values of $R_t$, or alternatively, the matrix $(R_t L_{xyz})$ may be post-multiplied by the appropriate values of $R^t_w$.

In the third alternative embodiment, the compressed data (singular vectors $L_{fi}$ and $R^t_{fi}$) are expanded into two-dimensional form for one, multi-lead ECG heartbeat. This process continues until data for all of the ECG heartbeats have been expanded.

Display Function

Figure 22:
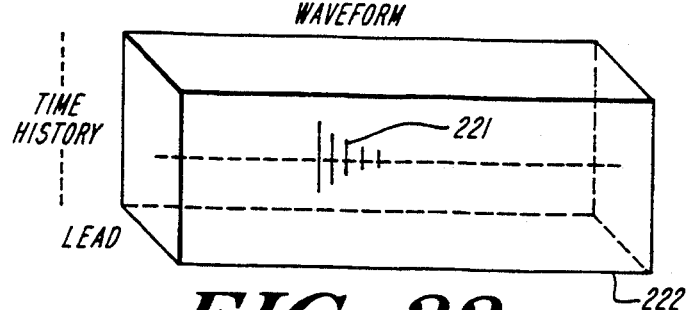
FIG. 22 is a three-dimensional, transparent display of the enhanced ECG data.

Referring to FIG. 22, after data enhancement, the data is displayed by the Display Function 66. In the preferred embodiment of the present invention, features of interest are displayed in the form of opaque objects 221 within an otherwise transparent cube 222 on an operator interface screen. Features not of interest may similarly be displayed. The operator can interactively rotate the three-dimensional transparent cube through various angles.

The three-dimensional cube can be rotated and displayed from different perspectives. The transparent cube contains enhanced and thresholded three-dimensional data, and displays features in a true spatial-temporal format. In other embodiments, the enhanced data may be squared, or otherwise modified before thresholding. This type of display is not possible in prior art systems which do not eliminate interference and noise, or correlate enhanced data across three dimensions.

The screen display includes time history, waveform segment, and ECG-lead cursors, which together allow a diagnostician to freely "travel" through the cube, displaying the ECG data at any time, waveform segment and ECG lead. In addition, the diagnostician can use these cursors to control the display of "slices," or planes, through the cube.

Figure 23:
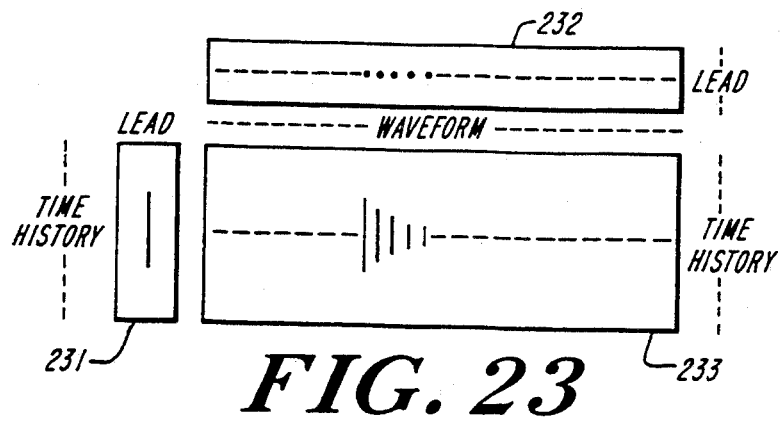
FIG. 23 shows time-history displays of the enhanced ECG data.

Referring to FIG. 23, the diagnostician can display these slices, or planes, in the ECG data cube in a set of multiple planar displays, including a time-history by ECG-lead display 231, an ECG-lead by waveform structure display 232, and a time-history by waveform structure display 233. In alternative embodiments of this format, the "slices" may present the enhanced data without thresholding, thereby displaying enhanced features against an otherwise opaque background.

In the present invention, additional displays are used to illustrate individual singular vectors, or sets of singular vectors. Other displays are used to illustrate the frequency spectra of the singular vectors, or in the case of the right singular vectors, spectrogram displays.

In alternative embodiments, a "movie" time history of ECG-data received for each time interval is displayed by thresholding and rapidly expanding the compressed data into its full, three-dimensional form and displaying the data in a time sequence of a growing transparent ECG data cube. As new ECG data is added to the top of the data cube, older time history data is dropped off the bottom of the data cube.

In an alternative embodiment, a movie display of enhanced data against an opaque background may be displayed as if one were rapidly "slicing" through the ECG data cube.

In an alternate embodiment, the compressed ECG data is transmitted to a remote location and expanded for viewing by a medical technician at the remote location.

While the foregoing invention has been described with reference to particular embodiments, it should be understood that various modifications and alterations will occur to those skilled in the art. Such modifications and alterations are intended to fall within the scope of the appended claims. Such modifications and alterations include implementing the invention with other multivariate data, including RF data, seismic data, other communication data, and medical imaging data.

In view of the foregoing, I claim:

1. A method of analyzing an electrocardiographic (ECG) signal, for determining diagnostic information comprising:
    analyzing the ECG signal to determine enhanced predetermined characteristics of the ECG signal according to the steps of,
    extracting data relating to said signals as received by an ECG monitoring system;
    embedding said data into a data matrix;
    compressing said data matrix into a compressed-data-form;
    modifying selected data values in said compressed-data-form based on a function of said data values in said compressed-data-form;
    expanding said compressed-data-form to an enhanced data matrix that contains data representing said enhanced predetermined characteristics.
    determining from said enhanced data matrix said diagnostic information.

2. The method of claim 1, wherein the method further includes a displaying step for displaying said enhanced data matrix on a display screen to show said characteristics.

3. The method of claim 1, wherein said compressing step further including decomposing said data matrix into singular vectors and singular values.

4. The method of claim 3, wherein at least one said singular vector is modified by said modifying step.

5. The method of claim 3, wherein at least one said singular value is modified by said modifying step.

6. The method of claim 3, wherein the method further includes the step of saving at least one subspace of said compressed-data-form in a historical database.

7. The method of claim 3, wherein the method further includes modifying said data matrix by multiplying at least a portion of said data matrix by a singular vector.

8. The method of claim 3, wherein the method further includes partitioning said compressed-data-form into subspaces.

9. The method of claim 8, wherein said compressed-data-form is partitioned into subspaces on the basis of a function of said singular values.

10. The method of claim 8, wherein said compressed-data-form is partitioned into subspaces on the basis of a function of its singular vectors.

11. The method of claim 1, wherein the method further includes the step of saving at least a portion of said compressed-data-form in a historical database.

12. The method of claim 11, wherein the method further includes the step of concatenating said historical database with said data matrix before compressing said data matrix.

13. The method of claim 11, wherein the method further includes the step of concatenating said historical database with said compressed-matrix-form after compressing said data matrix.

14. The method of claim 11, wherein the method further includes modifying said historical database before saving said database.

15. The method of claim 1, wherein said compressing step further includes:
    partitioning said data signals into at least two two-dimensional data matrices;
    concatenating said two-dimensional data matrices along a common dimension to form a concatenated two-dimensional data matrix; and
    decomposing said concatenated two-dimensional data matrix into singular vectors and singular values, with said compressed matrix form including said singular vectors and singular values.

16. The method of claim 1, wherein said compressing step further includes:
    partitioning said data signals into at least a first two-dimensional data matrix and a second two-dimensional data matrix;
    decomposing said first two-dimensional data matrix into first singular vectors and first singular values;
    concatenating said first singular vectors and said first singular values with said second two-dimensional data matrix; and
    decomposing said concatenated second two-dimensional data matrix into second singular vectors and second singular values, with said compressed-matrix form including said second singular vectors and said second singular values.

17. The method of claim 1, wherein said compressing step further includes:
    partitioning said data signals into at least a first two-dimensional data matrix and a second two-dimensional data matrix;
    decomposing said first two-dimensional data matrix into first singular vectors and first singular values;
    decomposing said second two-dimensional data matrix into second singular vectors and second singular values;
    concatenating said first singular vectors with said second singular vectors to form concatenated singular vectors; and decomposing said concatenated singular vectors into final singular vectors and final singular values, with said compressed-matrix form including said final singular vectors and said final singular values.

18. The method of claim 1, said compressing step further including decomposing said data matrix into eigenvectors and eigenvalues.

19. The method of claim 1, wherein said data matrix is three-dimensional.

20. The method of claim 19, wherein one of said dimensions is ECG lead.

21. The method of claim 19, wherein one of said dimensions is heartbeat time history.

22. The method of claim 19, wherein one of said dimensions is composed of waveform segments.

23. The method of claim 1, wherein said data matrix contains data relating to a function of the amplitude of said signals.

24. The method of claim 1, wherein said method further includes scaling said information in said data matrix by multiplying said information at a selected location in said multi-dimensional data matrix by a data coefficient associated with said location.

25. The method of claim 1, wherein the method further includes the step of displaying said enhanced data matrix as an opaque data cube with said enhanced data signals being displayed as objects within said data cube.

26. The method of claim 25, wherein the method further includes the step of selecting portions of said transparent data cube display and displaying said selected portions as two-dimensional data.

27. A method of determining the presence or absence of a predetermined level of high frequency spectral energy in the late QRS signal of an electrocardiograph signal, comprising the steps of:
extracting data relating to said electrocardiograph signal as received by an ECG monitoring system;
embedding said data into a data matrix;
decomposing said data matrix into singular vectors;
segmenting said singular vectors into a series of time intervals;
transforming said segmented singular vectors into a corresponding power spectra form; and
indicating the presence of ventricular late potentials by determining whether said predetermined level of spectral energy is present in said spectra form.

28. The method of claim 27 including the step of alerting an attendant when the presence of ventrical late potentials is indicated.

29. A system for analyzing an electrocardiograph signal, and for determining diagnostic information therefrom comprising:
means for analyzing said ECG signal to determine enhanced predetermined characteristics thereof,
means for extracting data signals relating to said signals as received by an ECG monitoring system;
means for embedding said data into a data matrix;
means for compressing said data matrix into a compressed-data-form;
means for modifying selected data values in said compressed-data-form based on a function of said data values in said compressed-data-form;
means for expanding said compressed-data-form to an enhanced data matrix that contains data representing said enhanced predetermined characteristics,
means for determining said diagnostic information from said enhanced data matrix.

30. The system of claim 29, wherein the system further includes means for displaying said enhanced data matrix on a display screen with said display showing said characteristics of said signal-generating objects.

31. The system of claim 29, wherein said means for compressing further including means for decomposing said data matrix into singular vectors and singular values.

32. The system of claim 31, wherein at least one said singular vector is modified by said modifying means.

33. The system of claim 31, wherein at least one said singular value is modified by said modifying means.

34. The system of claim 31, wherein the system further includes means for modifying said data matrix by multiplying at least a portion of said data matrix by a singular vector.

35. The system of claim 31, wherein the system further includes means for partitioning said compressed-data-form into subspaces.

36. The system of claim 35 wherein said compressed-data-form is partitioned into subspaces on the basis of a function of said singular values.

37. The system of claim 35 wherein said compressed-data-form is partitioned into subspaces on the basis of a function of its singular vectors.

38. The system of claim 35, wherein the system further includes means for saving at least one subspace of said compressed-data-form in a historical database.

39. The system of claim 29, wherein the system further includes means for saving at least a portion of said compressed-data-form in a historical database.

40. The system of claim 39, wherein the system further includes means for concatenating said historical database with said data matrix before compressing said data matrix.

41. The system of claim 39, wherein the system further includes means for concatenating said historical database with said compressed-matrix-form after compressing said data matrix.

42. The system of claim 39, wherein the system further includes means for modifying said historical database before saving said database.

43. The system of claim 29, wherein said means for compressing further includes:
means for partitioning said data signals into at least two two-dimensional data matrices;
means for concatenating said two-dimensional data matrices along a common dimension to form a concatenated two-dimensional data matrix; and
means for decomposing said concatenated two-dimensional data matrix into singular vectors and singular values, with said compressed matrix form including said singular vectors and said singular values.

44. The system of claim 29, wherein said means for compressing further includes:
means for partitioning said data signals into at least a first two-dimensional data matrix and a second two-dimensional data matrix:
means for decomposing said first two-dimensional data matrix into first singular vectors and first singular values;
means for concatenating said first singular vectors and said first singular values with said second two-dimensional data matrix; and
means for decomposing said concatenated second two-dimensional data matrix into second singular vectors and second singular values, with said compressed-matrix form including said second singular vectors and said second singular values.

45. The system of claim 29, wherein said means for compressing further includes:
   - means for partitioning said data signals into at lease a first two-dimensional data matrix and a second two-dimensional data matrix;
   - means for decomposing said first two-dimensional data matrix into first singular vectors and first singular values;
   - means for decomposing said second two-dimensional data matrix into second singular vectors and second singular values;
   - means for concatenating said first singular vectors with said second singular vectors to form concatenated singular vectors; and
   - means for decomposing said concatenated singular vectors into final singular vectors and final singular values, with said compressed-matrix form including said final singular vectors and said final singular values.

46. The system of claim 29, wherein said means for compressing further including means for decomposing said data matrix into eigenvectors and eigenvalues.

47. The system of claim 29, wherein said data matrix is three-dimensional.

48. The system of claim 47, wherein one of said dimensions is ECG lead.

49. The system of claim 47, wherein one of said dimensions is heartbeat time history.

50. The system of claim 47, wherein one of said dimensions is waveform segments.

51. The system of claim 29, wherein said data matrix contains data relating to a function of the amplitude of said signals.

52. The system of claim 29, wherein said system further includes means for scaling said information in said data matrix by multiplying said information at a selected location in said multi-dimensional data matrix by a data coefficient associated with said location.

53. The system of claim 29, wherein said system includes means for displaying said enhanced data matrix as a transparent data cube wherein said data signals are displayed as opaque objects within said transparent data cube.

54. The system of claim 53, wherein the system further includes means for selecting portions of said transparent data cube display and means for displaying said selected portions as two-dimensional data.

* * * * *